(12) United States Patent
Henderson et al.

(10) Patent No.: US 6,824,522 B2
(45) Date of Patent: Nov. 30, 2004

(54) HARDENABLE ORTHOPAEDIC SUPPORTS

(75) Inventors: Wendy Henderson, Ventura, CA (US); Michael Campos, Camarillo, CA (US); Walter Doubleday, Jupiter, FL (US); Joseph Iglesias, Thousand Oaks, CA (US); Tracy Grim, Tulsa, OK (US)

(73) Assignee: Royce Medical Company, Camarillo, CA (US)

( * ) Notice: Subject to any disclaimer, the term of this patent is extended or adjusted under 35 U.S.C. 154(b) by 189 days.

(21) Appl. No.: 10/136,023

(22) Filed: Apr. 29, 2002

(65) Prior Publication Data

US 2002/0193718 A1 Dec. 19, 2002

Related U.S. Application Data

(63) Continuation-in-part of application No. 09/823,968, filed on Mar. 29, 2001, now Pat. No. 6,482,167.

(51) Int. Cl.[7] ................................................. A61F 5/00
(52) U.S. Cl. ...................................... 602/6; 602/5; 602/8
(58) Field of Search .................................... 602/5, 6, 8

(56) References Cited

U.S. PATENT DOCUMENTS

| | | | | |
|---|---|---|---|---|
| 4,019,506 A | * | 4/1977 | Eschmann | |
| 4,479,490 A | * | 10/1984 | Dedo | |
| 5,732,713 A | * | 3/1998 | Duback et al. | |
| 6,007,505 A | * | 12/1999 | Grim et al. | |

* cited by examiner

Primary Examiner—Nicholas D. Lucchesi
Assistant Examiner—Lalita M Hamilton
(74) Attorney, Agent, or Firm—Oppenheimer Wolff & Donnelly LLP

(57) ABSTRACT

An orthopaedic support assembly is formed of a flexible material impregnated with a hardenable material, e.g. a water-hardenable urethane. The orthopaedic support may include an outer layer of napped material, e.g., an unbroken loop material, that reduces migration of the hardenable material. The orthopaedic support may also include an inner layer of foam padding to increase the comfort of the patient.

27 Claims, 9 Drawing Sheets

HARDENABLE ORTHOPAEDIC SUPPORTS

CROSS-REFERENCE TO RELATED APPLICATION(S)

This patent application claims priority to, and is a continuation-in-part of, U.S. patent application Ser. No. 09/823,968, filed Mar. 29, 2001, now U.S. Pat. No. 6,482,167 incorporated herein by reference in its entirety.

TECHNICAL FIELD

This invention relates to improved hardenable orthopedic supports, e.g., splints or casts.

BACKGROUND

Orthopaedic supports are used to provide structural support and/or limit movement of a portion of a patient's anatomy. Hardenable splints and casts are commonly formed by wrapping or otherwise positioning layers of a strip or "tape" of hardenable material about the afflicted area and allowing the material to harden in place. Gauze coated with calcined gypsum has been used for many years, but more modern hardenable supports are formed with other fabrics (e.g., knitted fiberglass) and employ hardenable organic resins instead of calcined gypsum.

For example, U.S. Pat. No. 4,996,979, granted Mar. 5, 1991, and U.S. Pat. No. 4,683,877, granted Aug. 4, 1987 disclose water-hardenable organic resins used in this context. Other hardenable resins used in this field include epoxies and UV-curable materials.

When using such tapes in forming orthopaedic supports, multiple layers of the tape are wrapped about or positioned on the limb or other affected part of the patient's anatomy. In applying the tape to form a cast, for example, care must be taken to firmly engage the layers during the exotherm portion of the setting period to ensure unitary bonding of the entire layered cast or assembly. This step requires care and expertise to ensure that the layers are properly bonded without causing pain or discomfort to the patient, e.g., when forming a cast around a broken limb. Applying fiberglass tape to form a water-hardenable core of a splint or support requires considerable skill and practice to form splints or supports of varying thickness which may be required or which may be desirable for certain applications. Thus, for example, when a cast is to be provided for a foot and lower leg, it may be desirable to have greater thickness in the lower portion of the cast, and a lesser thickness in the vicinity of the shin or the calf of the user. Applying layers of fiberglass cloth requires considerable experience to form a varying thickness layered cast or support which will have proper inter-layer bonding and strength.

Not all hardenable orthopaedic supports are formed by winding an elongate strip of tape around the limb or other anatomical structure. For example, U.S. Pat. No. 6,186,966, granted Feb. 13, 2001 and entitled "Hardenable Orthopaedic Support With Improved Configuration," the entirety of which is incorporated herein by reference, suggests a support which, in one configuration, may be pre-shaped to be reliably placed on an anatomical structure, e.g., a palm, wrist and forearm. Certain embodiments include a pair of spaced interwoven layers formed of high-strength materials with an open matrix of filaments or threads interconnecting the layers. The support is flexible and can conform to the intended anatomical structure without forming wrinkles, which lend the product an unsightly appearance and can lead to patient discomfort. This approach also avoids the necessity to wrap plural layers of tape, contour the tape to appropriately fit the limb, and compress the layers together to avoid delamination.

Another problem encountered in this field is the fraying of the edges of material when fabric, such as fiberglass fabric, is cut. When the hardenable resin cures, the frayed edges may harden and may cause patient discomfort or abrade adjacent soft tissue. This difficulty often plagues orthopaedic supports, including pre-shaped hardenable supports. Typically, the material which carries the resin is coated in a continuous process, e.g., by spraying or dipping the material in a bath of the resin and squeezing out some of the excess resin between a pair of rollers. Many commercially available hardenable resins, e.g., urethane resins, are viscous, tacky fluids which may stick to a die or other cutting equipment, making it very difficult to cut desired shapes. As a consequence, most commercially successful hardenable orthopaedic supports to date are sold in the form of continuous tape or rectangular swatches of a predetermined size, which must then be arranged on the patient's limb.

Some hardenable orthopaedic supports employ an inner structure which carries the hardenable resin and one or more external layers. For example, one of the splint structures suggested in U.S. Pat. No. 6,186,966, noted above, includes a water-pervious outer layer and an inner layer adapted to keep the patient's skin dry. Water-hardenable orthopaedic supports are often stored and shipped in sealed, water-impervious packages, e.g., a plastic blister pack. The resin is in contact with the our layers during storage and shipment and, over time, resin can migrate through one or both of the outer layers. When this product is removed from the package, wetted (if necessary) and applied to the patient, the resin on the outside of the product can harden on the physician's or technician's hands and can harden on the patient's skin. This can also lead to an irregular, mottled surface, making the support less attractive and lending a less professional appearance.

SUMMARY

Aspects of the present invention provide orthopaedic supports and methods of manufacturing such supports. One embodiment provides a hardenable orthopaedic support assembly which includes a flexible first layer having an outer edge portion, a second layer of napped material, and a blank located between the first layer and the second layer. The second layer of napped material has a napped side and an outer edge portion. The outer edge portion of the second layer is at least partially attached to the outer edge portion of the first layer. The blank comprises a flexible material which is at least partially impregnated with a hardenable material.

A hardenable orthopaedic support assembly in accordance with a more specific embodiment of the invention may include a layer of padding material having an outer edge portion, a layer of napped material, and a blank located between the layer of napped material and the layer of padding material. The layer of napped material may have a substantially smooth side, a napped side, and an outer edge portion. The substantially smooth side may face away from the layer of padding material and the outer edge portion of the layer of napped material and the outer edge portion of the layer of padding material may be at least partially attached. The blank may comprise a flexible material which is at least partially impregnated with a hardenable material. In one application, the layers of padding material and napped material and the blank are shaped to cover at least a portion of a patient's anatomy. The shape may include two or more lobes and one or more narrowed joining regions, the lobes being adapted to be located near a particular part of the patient's anatomy.

Other embodiments of the invention provide various orthopaedic methods. In one such method, an integral double layer fabric is formed, the double layer fabric having spaced interwoven layers and an open-work matrix of filaments interconnecting the interwoven layers. The fabric may include at least some high strength filaments and the open-work matrix may be permeable to an activating agent. The open-work matrix of filaments and the two surface layers may be impregnated with a hardenable material while retaining the permeability of the matrix to an activating agent. The double layer fabric may be enclosed between two layers of material, wherein at least one of the materials is a napped material. In one particular configuration, the napped material has a napped side which is oriented to face the blank. The two layers are connected substantially near their edges to completely enclose the double layer fabric and form a support structure.

DETAILED DESCRIPTION

Figures 1A, 1B, 1C, 1D:
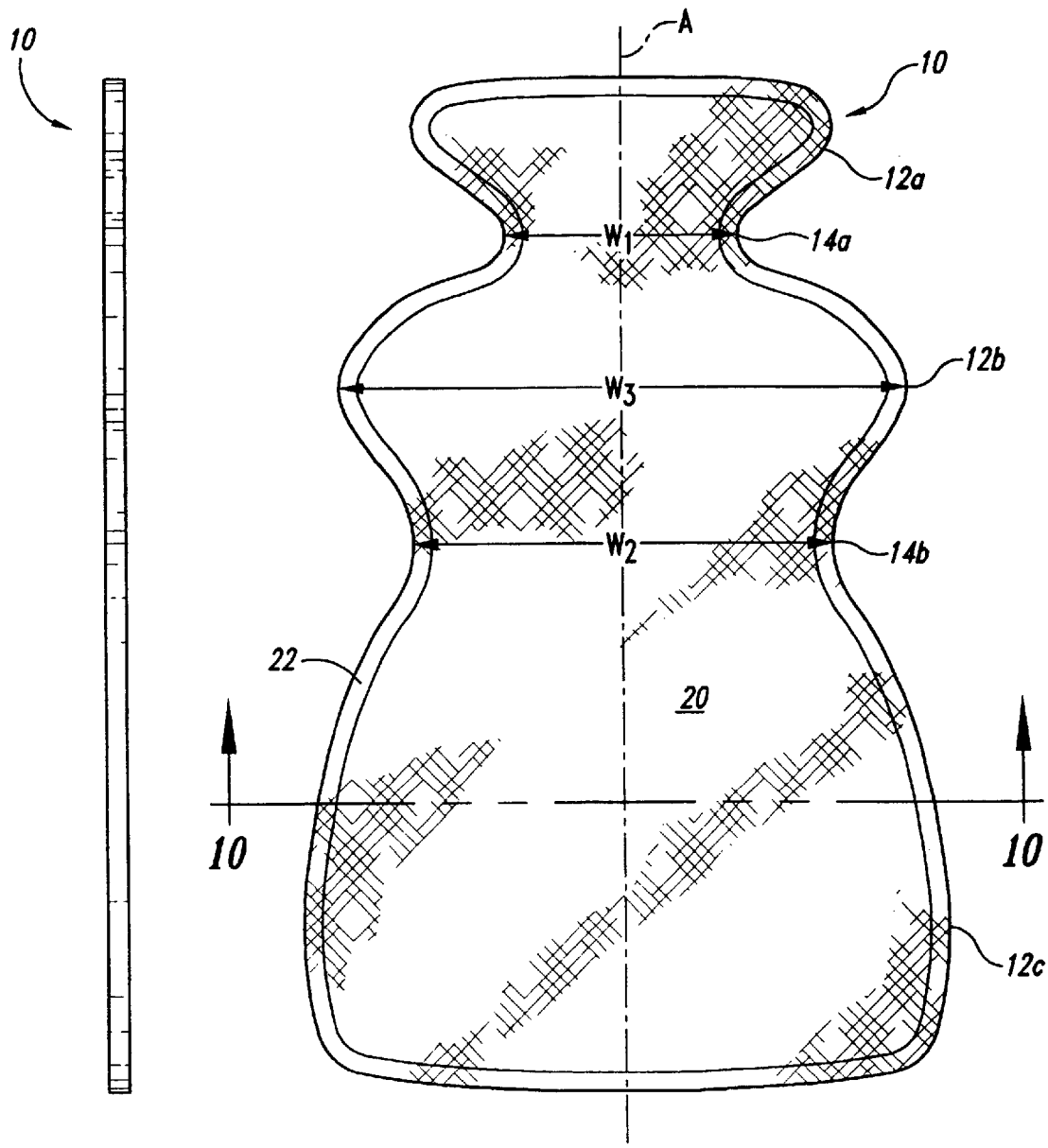
FIGS. 1A–D are plan, left, top, and bottom views, respectively, of an orthopaedic support for use in a splint or cast for an extremity of a patient in accordance with an embodiment of the invention.

Various embodiments of the present invention provide orthopaedic supports, subassemblies for such supports, methods of manufacturing orthopaedic supports, and apparatus for use in manufacturing orthopaedic supports. The following description provides specific details of certain embodiments of the invention illustrated in the drawings to provide a thorough understanding of those embodiments. It should be recognized, however, that the present invention can be reflected in additional embodiments and the invention may be practiced without some of the details in the following description. To facilitate understanding and readability, a few select shapes will be discussed, followed by a more detailed analysis of the internal structure of certain embodiments, and methods in accordance with other embodiments are then described.

In one embodiment, a hardenable orthopaedic support for providing orthopaedic care to a patient is disclosed. In this embodiment, the support comprises a layer of padding material having an outer portion, a layer of napped material, and a blank made of a flexible, permeable material. The layer of napped material may have a substantially smooth side, a napped side, and an outer edge portion, where the napped side faces the blank. The outer portions of the layers of napped material and padding material may be at least partially attached. The blank may be at least partially impregnated with a hardenable material, and the blank may be located between the layer of napped material and the layer of padding material.

In another embodiment, a method of using a hardenable orthopaedic support is disclosed. In this embodiment, the method comprises forming a blank, the blank being at least partially permeable to an activating agent and impregnating at least part of the blank with a hardenable material which will harden in response to application of the activating agent. The method may also comprise enclosing the blank between two layers of material, wherein at least one of the materials is a napped material, wherein the napped material has a napped side facing the blank. The method may also comprise connecting the two layers substantially near their edges to completely enclose the blank and form a support structure.

Exemplary Designs

FIGS. 1A–D show an orthopaedic support 10 in accordance with one embodiment for providing splinting or casting action for an extremity of a patient. The orthopaedic support 10 shown in FIG. 1 is particularly well-adapted for use with an upper extremity, such as a patient's arm, and includes three laterally-extending lobes 12a–c separated by two narrowed joining regions 14a–b. In this particular embodiment, the lobes 12 and joining regions 14 are generally symmetrical about a longitudinally-extending axis A. In the illustrated embodiment, each of the lobes 12 have a width (measured transversely at its widest point) at least about 1.3 times the width (measured transversely at its narrowest point) of the or each contiguous joining region 14. In one embodiment, each of the lobes 12 has a width at least about 1.5 times the width of at least one contiguous joining region 14. In the support 10 of FIG. 1, the distal joining region 14a has a first width $W_1$, the proximal joining region 14b has a second width $W_2$, and middle lobe 12b has a third width $W_3$. The third width $W_3$ is at least about 1.3 times both the first width $W_1$ and the second width $W_2$ and is at least about 1.5 times the first width $W_1$.

The orthopaedic support 10 is designed to drape over a patient's limb and to minimize wrinkles in the final cast or splint, as wrinkles can cause pressure points and ultimately cause discomfort or injury to the patient. The support 10 also guides a medical professional in placing the support 10 on a patient, as each lobe 12 and joining region 14 corresponds to a particular part of a patient's anatomy. For example, the distal lobe 12a may extend about a portion of the patient's hand distal of the thumb; the distal joining region 14a may be aligned with the thumb to position the thumb and its web space between the distal and middle lobes 12a–b of the support 10; the middle lobe 12b may extend between the thumb and the wrist; the proximal joining region 14b may be aligned with the wrist to comfortably receive the ulnar styloid; and the proximal lobe 12c may extend proximally to at least partially encircle a length of the forearm.

In addition to facilitating positioning of the support 10 at the proper general location, the design shown in FIG. 1 enables articulation of the support 10 to better conform to each patient's anatomy. More specifically, the narrower joining regions 14 can accommodate more lateral torsion, e.g., bending of the axis A in FIG. 1A into a non-linear shape to better accommodate a patient's anatomy. In this regard, the shape of the support 10 can be flexed and contoured to meet the needs of each patient, unlike more conventional rectangular supports. The multi-lobed design of orthopaedic support 10 can also be beneficial in that the lobes may be sized to 'grab' more of a patient, and thus keep the support more stable, without causing the patient undue discomfort.

As explained in more detail below, the orthopaedic support 10 may be formed of a flexible and/or stretchable material, e.g., an impregnated, hardenable double-knit material as described in relation to FIGS. 10–13, to permit the support 10 to readily drape over a patient's limb. This draping ability and the multiple-lobed shape of the support 10 can reduce the likelihood of developing wrinkles in the final, hardened cast or splint. Unless great care and expertise is used in applying conventional tape-type splints, such splints can wrinkle fairly readily, creating pressure points that may cause the patient discomfort or injury.

Once properly positioned, the orthopaedic support 10 may be held in place by a temporary aide such as an elastic bandage, a hook-and-loop tape (e.g., VELCRO® tape), gauze, a bias stockinette, or any other suitable means. The natural draping effect of the support 10 can also help stabilize the support while wrapping the elastic bandage or applying any other temporary aide. The orthopaedic support 10 can be used alone or, as discussed below, may be used as a subassembly of a more complex support (e.g., support 15 of FIG. 12, which employs the device of FIG. 1 as a blank 10 within an envelope 50 having beneficial properties for some applications).

FIGS. 2–9 show several different orthopaedic supports in accordance with alternative embodiments. The orthopaedic supports 100–170 depicted in FIGS. 2–9 may be formed of similar materials and in similar methods to those outlined below, and may function similarly to the orthopaedic support 10 shown in FIG. 1 and described above. These alternative supports 100–170, however, are shaped differently from the support 10 of FIG. 1.

Figure 2:
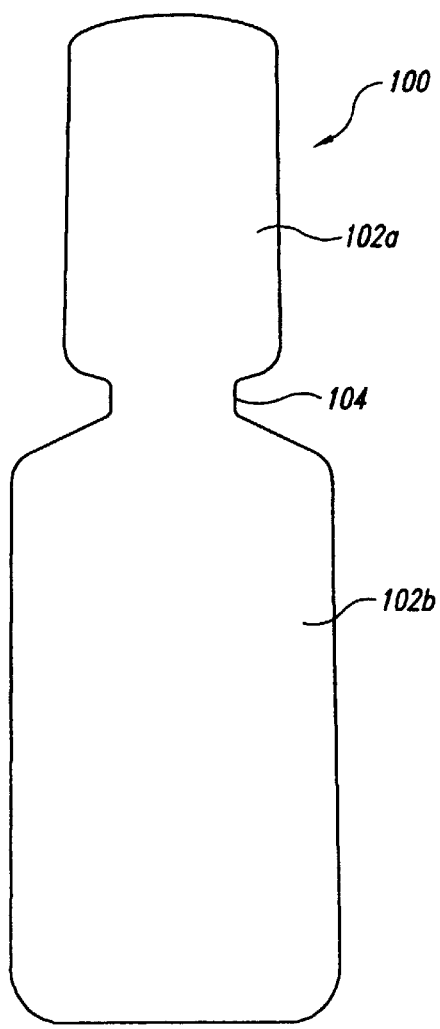
FIGS. 2–9 show alternative embodiments of orthopaedic supports for use in splints or casts for patients' extremities.

The orthopaedic support 100 of FIG. 2 has a pair of lobes 102a–b separated by a single narrow joining region 104. Such a 2-lobed design may be used to support an arm, but it may be more appropriate for other anatomical structures, e.g., a leg. Both of the lobes 102a–b have a width which is at least about 1.5 times the width of the joining region 104; in the particular illustrated shape, the distal lobe 102a has a width at least about 1.75 times the width of the joining region 104 and the proximal lobe 102b has a width at least about 2.5 times the width of the joining region 104.

Figure 3:
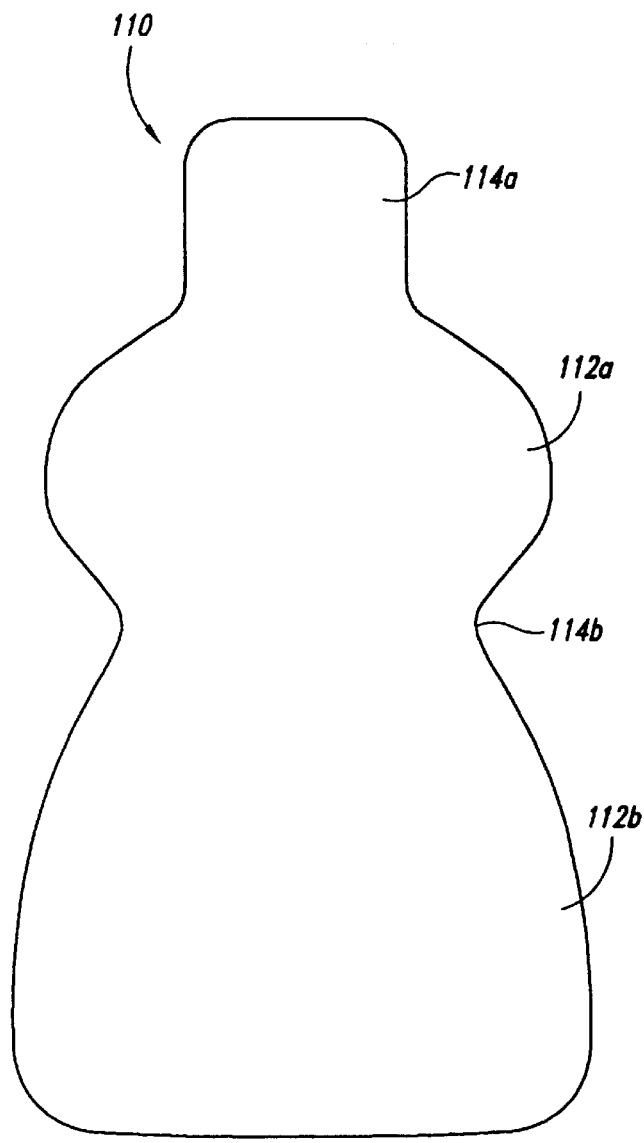
Figure 4:
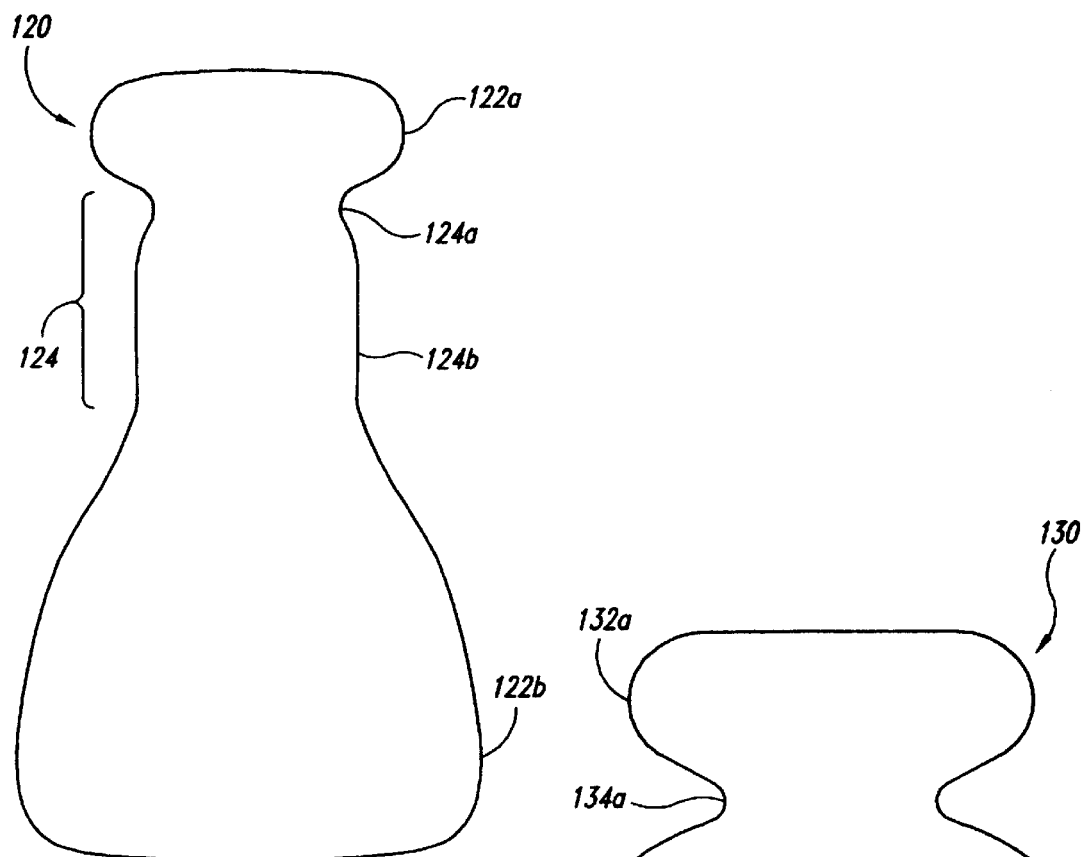
Figure 5:
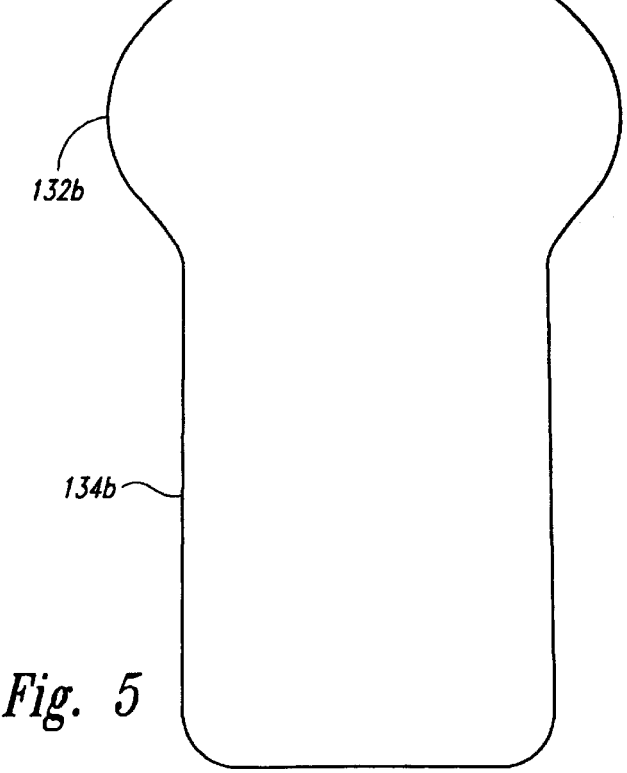
Figures 6, 7:
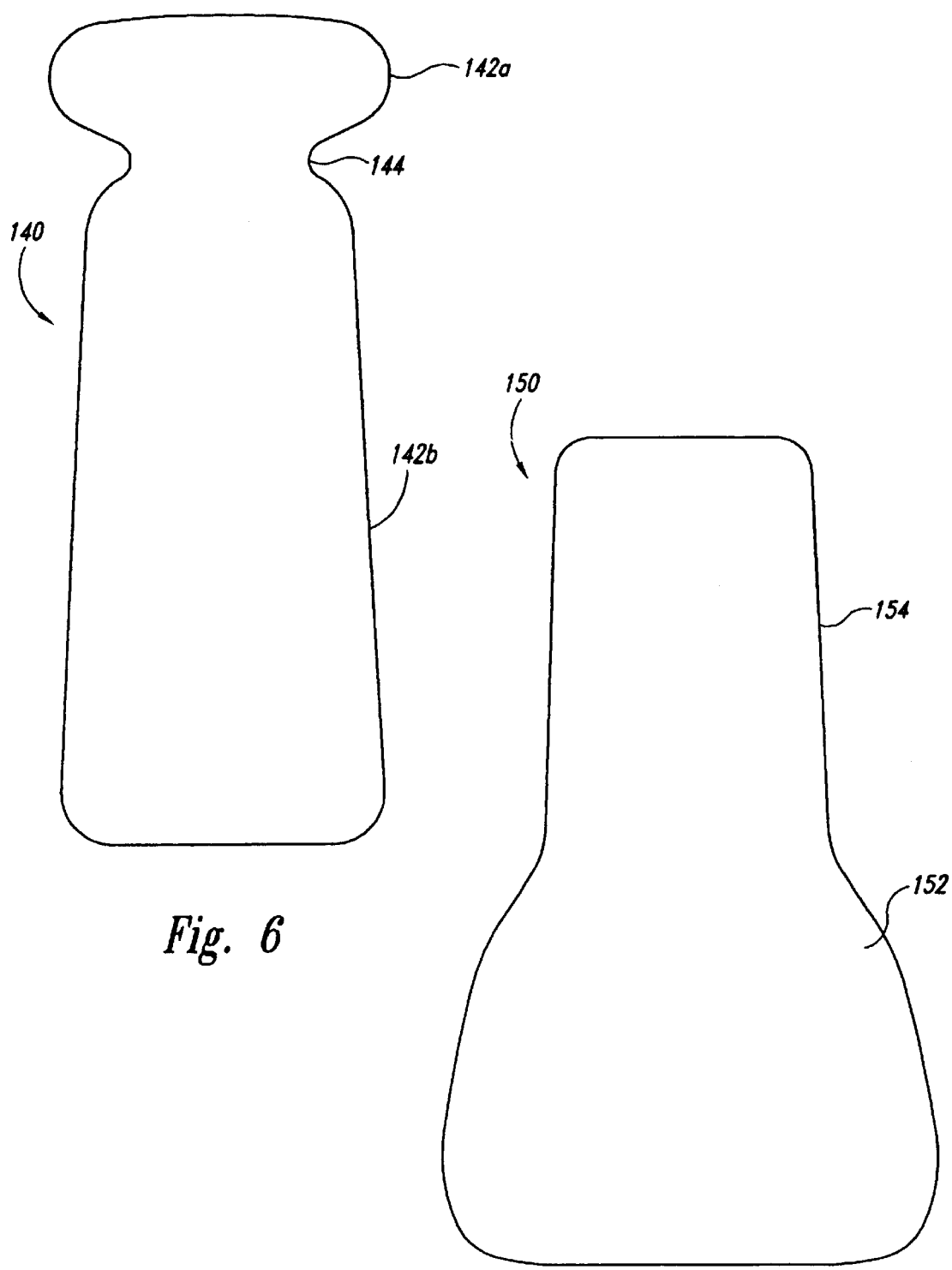

The orthopaedic support 110 of FIG. 3 has a pair of lobes 112a–b, a distal narrow length 114a which extends distally of the distal lobe 112a, and a narrow joining region 114b between the distal lobe 112a and the proximal lobe 112b. The orthopaedic support 120 of FIG. 4 has an elongate joining region 124 between a distal lobe 122a and a proximal lobe 122b. The joining region 124 in this embodiment has a proximal length 124b of substantially constant width and a narrowed neck 124a connecting the proximal length 124b to the distal lobe 122a. FIG. 5 illustrates an orthopaedic support 130 having a distal lobe 132a and a proximal lobe 132b separated by a narrow joining region 134a and a proximal length 134b which extends proximally from, and is narrower than, the proximal lobe 132b. In FIG. 6, orthopaedic support 140 includes a distal lobe 142a and an elongate proximal lobe 142b, which may be generally rectangular in shape or may taper outwardly in a proximal direction. A narrow joining region 144 may connect the two lobes 142.

Figure 8:
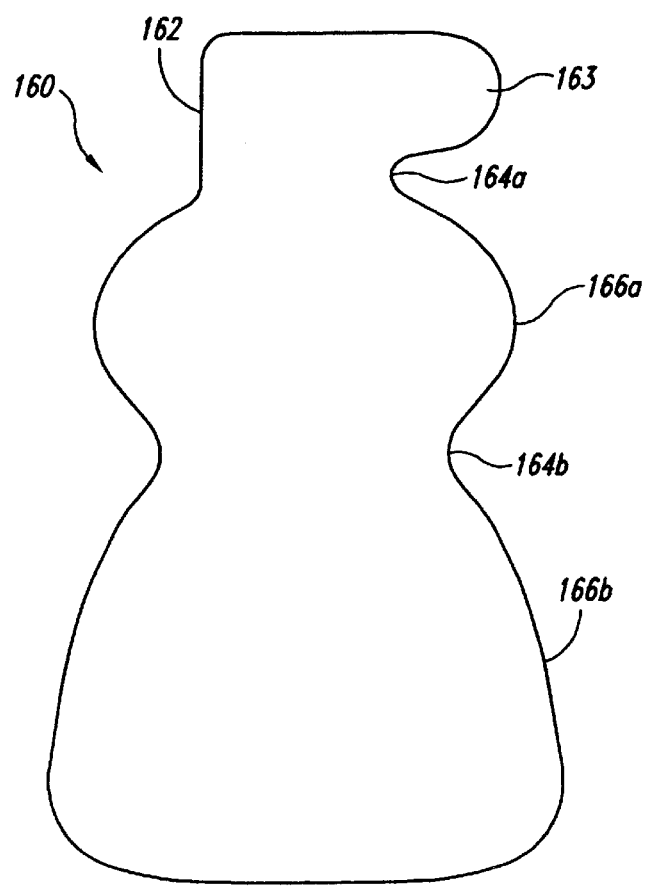
Figure 9:
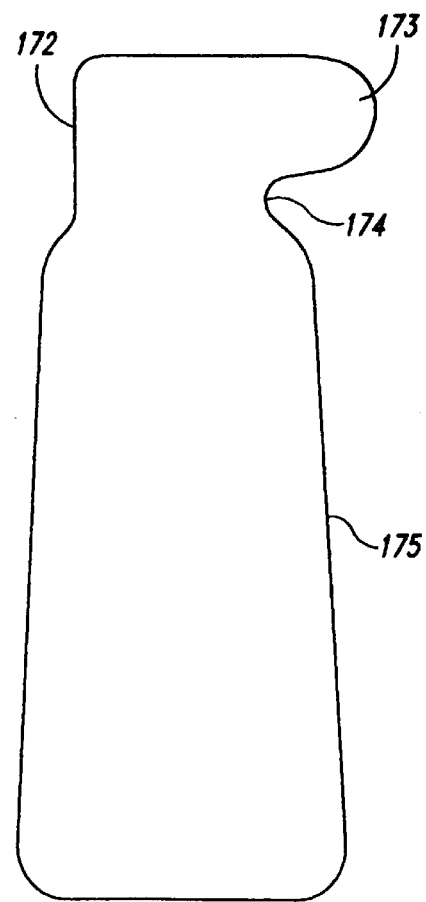

Unlike the multi-lobed designs of FIGS. 1–6, the orthopaedic support 150 of FIG. 7 has a single wide proximal region 152, which may flare out proximally, and a generally rectangular distal region 154, which is narrower than the proximal region 152. Although this shape does have utility, e.g., for supporting lower extremities, it is not considered to be as beneficial as some of the previously-described embodiments, e.g., the support 10 of FIG. 1. FIG. 8 illustrates a design which has a distal length 162 with a laterally-extending tongue 163, a distal joining region 164a, a distal flared region 166a, a proximal joining region 164b, and a proximal flared region 166b. The orthopaedic support 170 of FIG. 9 has a distal length 172 with a laterally extending tongue 173, a narrow joining region 174, and an elongate proximal region. The asymmetrical designs of FIGS. 8 and 9 can be advantageous in some applications, but may not be as widely useful as the symmetrical design shown in FIG. 1, for example.

Exemplary Structures

Referring back to FIG. 1, the orthopedic support 10 may include a centrally-disposed structural region 20 and a peripheral region 22 extending outwardly beyond the structural region. In the illustrated embodiment, the peripheral region 22 extends about the entire periphery of the structural region 20 and has a substantially constant width about the entire periphery. As a consequence, the structural region 20 has the same general multi-lobed, nonrectangular shape as the entire support 10. In other embodiments, the peripheral region 22 extends around only a portion of the circumference of the structural region 20, with the structural region 20 extending to the edge of the support 10 along the remainder of its circumference. The width of the peripheral region 22 may be varied as desired. It is anticipated that a peripheral region 22 having a width of about ⅛ inch to about ½ inch, e.g., about ⅛ inch to about ¼ inch, will suffice for most applications.

Some or all of the support 10 may be impregnated with a hardenable material. The hardenable material is adapted to harden in response to a specific activating agent. For example, a water-hardenable material, such as a prepolymerized urethane material, may be employed. When the water-hardenable material contacts water, it will harden. Water-hardenable materials are well known, and have been used heretofore in orthopaedic devices. See, for example, U.S. Pat. Nos. 4,996,979 and 4,683,877, both of which are incorporated herein in their entirety. As is known in the field, other hardenable materials may instead be used, such as UV-curable resins or one component of a two-component epoxy.

In one embodiment, the structural region 20 of the support 10 is impregnated with the hardenable material, but the peripheral region may remain free of the hardenable material. As a consequence, when the support 10 is in place and the water or other agent is used to activate the hardenable material, the structural region will harden to support the limb or other anatomy to which it is applied. Because the peripheral region 22 is free of the hardenable material, the peripheral region will not harden when contacted with water. As a consequence, the peripheral region may flex with the patient's movements, both increasing patient comfort and avoiding abrasion or other damage which can occur with the stiff projecting edges of conventional casting tapes or the like.

Figure 10:
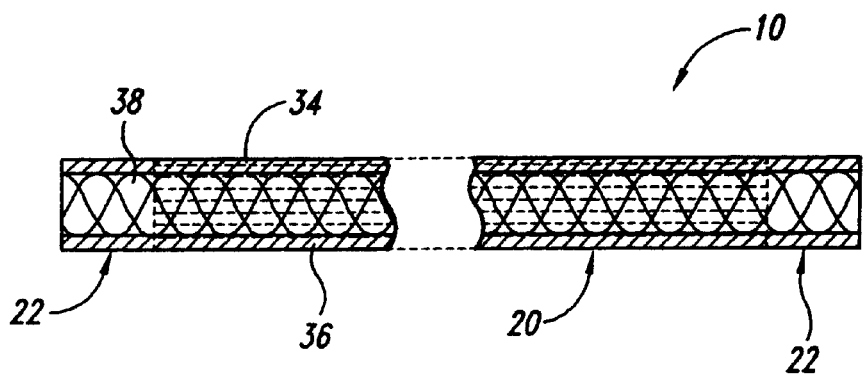
FIG. 10 is a cross-sectional view of the orthopaedic support of FIG. 1 taken along line 1—1 of FIG. 1A.

A variety of cross-sectional structures may be suitable for the orthopaedic support 10 of FIG. 1. FIG. 10 is a schematic cross-sectional view of the orthopaedic support 10 in one such embodiment taken along line 10—10 of FIG. 1. As shown in FIG. 10, the support 10 may comprise a double-knit fabric 32 including surface knits 34 and 36 and spacer yarns 38. The surface knits 34 and 36 can be of the same or different knit patterns. These patterns can range anywhere from smooth, essentially continuous surfaces to meshes and other more complex knits. They may be knit from materials such as polyester, nylon, and various high strength fibers, including fiberglass, aramid and/or carbon fibers. The spacer yarns 38 keep the surface knits 34 and 36 a specific distance apart, and allow for individual surface movement. The spacer yarns 38 may comprise monofilament yarns, but can also be multi-filament yarns. The spacer yarns 38 may be made from polyester, nylon, or other thermoplastic materials that can be drawn into a yarn of the desired diameter; they may also be made from glass or aramid fibers. The thickness of the double-knit-type material may range from about $\frac{1}{16}$-inch thickness to about $\frac{3}{4}$-inch thickness, with about $\frac{1}{8}$-inch to about $\frac{3}{8}$-inch being preferred. In another embodiment (not shown), a permeable foam material may be used instead of the spacer yarns, with the surface knits 34 and 36 being formed as separate knit layers and subsequently bonded to opposite faces of the foam, e.g., with an adhesive.

In one embodiment, the double-knit type material includes a substantial proportion of high strength materials such as fiberglass, aramid fibers such as KEVLAR, or carbon fibers. It is noted that fiberglass, KEVLAR, and carbon fibers may all have tensile strengths which are an order of magnitude or more greater than the tensile strength of many thermoplastics, e.g., LDPE. More generally, high-strength fibers used in certain embodiments have tensile strengths greater than 500 MPa, e.g., 1,000 Mpa or greater. They also may be fairly stiff. To better accommodate this stiffness, the double-knit type fabric may be of a fairly loose weave.

In one suitable double-knit fabric, the upper layer 34 and the lower layer 36 are formed of fiberglass and the open matrix of interconnecting fibers 38 is formed of 30 denier polyester monofilament, a thermoplastic material. The fiberglass constitutes about 71% by weight (wt. %) of the assembly, and the polyester comprises the remaining 29 wt. %. Using this type of assembly, with a relatively stiff, high-strength material and a thermoplastic material, the double-knit type fabric may be concurrently cut and heated to melt and fuse the thermoplastic into the fiberglass, thereby limiting fraying or unraveling of the cut edges. Ultrasonic cutting and sealing equipment to accomplish the foregoing is available, for example, from Branson Ultrasonics Corp., 41 Eagle Road, Danbury, Conn. 06813-1961. More generally, the amount of the fiberglass or other stiffer, high-strength filaments may range from 10 wt. % to 100 wt. % of the double-knit fabric, e.g., about 20 wt. % to 80 wt. %, with the remainder comprising any desired filaments to suit the application, with a thermoplastic better enabling the cut edge treatment described above.

Figure 11:
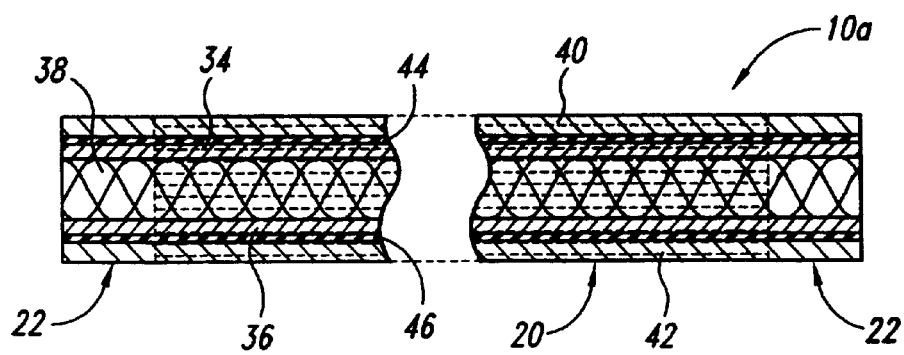
FIG. 11 is a cross-sectional view of a double-knit type material which may be employed in the fabrication of an orthopaedic support in one embodiment.

FIG. 11 schematically illustrates a modified embodiment of a support 10a that reinforces the double-knit fabric with glass knits or other high strength fabrics to increase their strength. In this particular embodiment, fiberglass fabric 40 and 42 may be bonded to the surface knits 34 and 36 by adhesive webs 44 and 46, respectively. This bonding could also be achieved by any other known technique such as by flame bonding, or by sewing, for specific examples. The lamination of the glass knit fabrics 40 and 42 to the double-knit material by the adhesive layers 44 and 46 also reduces fraying of the glass knit when the assembly is cut, and can help hold the entire assembly intact during subsequent operations.

Figure 12:
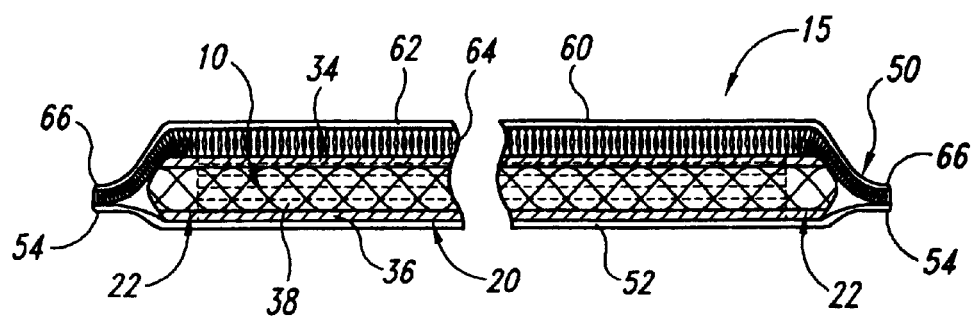
FIG. 12 is a cross-sectional view of central layer of double-knit type material reinforced by layers of high strength material which may be employed in the fabrication of an orthopaedic support in one another embodiment.

If so desired, the support 10 shown in FIG. 1 may be employed as a casting blank which is retained in an outer envelope. FIG. 12 illustrates an orthopaedic support 15 in accordance with one such embodiment. The support 15 includes a blank, illustrated as the support 10 of FIGS. 1 and 10, positioned in a flexible envelope 50. If so desired, the blank may have any other suitable structure. For example, the blank or central body material may comprise a reinforced double-knit material 10a as described in relation to FIG. 11, multiple layers of double-knit material, multiple layers of double-knit material separated by a foam laminate or other divider, foam material with a single-knit material attached to both sides (such as cast tape), a layer of foam without any fabric attached thereto, multiple layers of single-knit material. Instead of knit materials, woven materials, felted materials, or other nonwoven materials may be employed. In one particular embodiment, the blank 10 of FIG. 12 comprises a layer of a flexible, water-permeable foam material with at least a central support region of the foam being impregnated with a water-hardenable material.

The orthopaedic support 15 of FIG. 12 includes an exterior layer 60 and a interior layer 52 that together form an envelope 50 which may substantially encapsulate the blank 10. The exterior layer 60 is designed to be on the outside of the orthopaedic support 15 when applied, while the interior layer 52 is designed to be adjacent the patient's skin (and possibly separated by a fabric, bandage or other item). In one embodiment, the exterior layer 60 is made of a material having a relatively smooth external surface 62 and a lofty, internal nap 64. In certain embodiments, the exterior layer 60 comprises the loop-type material or hook material of a mating hook and loop-type fastening system, such as VELCRO®. In one suitable embodiment the exterior layer comprises an unbroken loop material ("UBL"), which may correspond to the "soft," "fuzzy" loop-type material of a mating hook and loop-type fastener. In one particular embodiment, the UBL comprises a flexible knit fabric which has one napped surface. The exterior layer 60 may be placed with the napped side 64 facing the blank 10 and the smoother backing 62 facing outwards. The exterior layer 60 may also be formed of any other napped material, e.g., a knitted material such as terrycloth. In this embodiment, the napped side of the material would be placed facing the blank 10. In another alternative embodiment, any suitably flexible and/or stretchable material with a high loft may be used, typically with a high loft side facing the blank 10. Napped materials, including unbroken loop materials, are available from sources such as Gehring Textiles Inc. of New York, N.Y.

The interior layer 52 may be made of foam padding, e.g., an open-cell polyurethane. Foam padding may provide comfort for the patient, as the interior layer 52 will likely be the layer touching the patient's anatomy. One skilled in the art will recognize that the interior layer 52 may be made of a wide variety of materials, such as fabric, UBL materials, napped materials, other padding, etc.

The exterior layer 60 and interior layer 52 may be bonded together at their outer edges 54, 66 by thermal welding, by permanent adhesive, by ultrasonic welding, stitching, or in any other desired manner. The bonding may be accomplished in successive spots or lines or may be continuous. The impregnated blank 10 is therefore contained within the envelope 50 between the exterior layer 60 and interior layer 52, which will inhibit migration or leaking of the resin during shipment and storage. In one embodiment, the blank 10 is placed between the exterior layer 60 and interior layer 52 immediately after being impregnated. Once the exterior layer 60 and interior layer 52 are bonded together, the orthopaedic support 15 may be sealed in a water vapor-impermeable package (not shown). Sealing the orthopaedic support 15 in the package quickly can reduce exposure to moisture contained in the air. If a UV-curable resin or the like is instead used to harden the support 10 once in place, the package need not be water vapor-impermeable, but it should be opaque to ultraviolet radiation.

The water vapor-impermeable package may be formed of metallized mylar, aluminum foil, or any known water vapor-impermeable material which will reduce the chances of premature activation and hardening of the urethane or other water-hardenable material which is impregnated into the blank 10. One suitable water vapor-impermeable sheet material comprises aluminum foil coated with plastic on both sides, available from Richmond Tech, Inc., 1897 Colton Avenue, Redlands, Calif. 92374-9797. This material has a low moisture vapor transfer rate of about 0.0006 grams per 100 square inches per day.

In one embodiment, the blank material is initially impregnated with the water-hardenable material, and then the entire soft good product, tape or blank, is packaged in a water vapor impermeable package. When it is time to apply the product to a patient, the package is opened, the product is immersed in water or water is applied to it, and the product is mounted onto the part of the anatomy requiring support or splinting. With the open-work matrix of the double-knit material, for example, rapid and thorough penetration of the water and activation of the urethane occurs. In the case of soft goods types of products, straps may be employed to mount the support firmly on the injured portion of the anatomy, water is applied or injected, and the water-hardenable material conforms to the configuration of the patient. In another embodiment, blanks may be immersed in water and promptly applied to the injured portion of the anatomy before the hardening occurs.

The use of a napped material prevents or slows down resin (or other hardenable material) migration over time. This effect appears to be stronger when the napped side of a napped material such as UBL is located adjacent a resin-impregnated material. As noted above, resin has a tendency to leak or migrate out of an orthopaedic support over time, such as during shipping or storage. When the orthopaedic support is ultimately activated, the resin that has leaked out may cause imperfections or protuberances on the outer surface of an orthopaedic support. It has been found that UBL is useful in preventing or retarding resin migration, even during long shipping or storage periods. By using a napped material such as UBL as an exterior layer 60, the orthopaedic support 15 of FIG. 12 also provides a smoother and cleaner outer surface on the finished support because of the smooth surface of the backing 62 of the napped material and the reduced migration of hardenable material therethrough.

The UBL material used in selected embodiments provides a smooth external surface with minimal wrinkles. The relatively smooth surface is inherent with many UBL materials, and the ability of UBL materials to stretch and flex reduces the number of unsightly wrinkles on the orthopaedic support 15. In addition, UBL materials are generally quick-drying, so that when the orthopaedic support 15 is, for example, immersed in water to activate the resin, the UBL material 60 (and thus the outside of the support 15) dries quickly. UBL materials are also relatively light and strong when compared to alternative materials, and are also more resistant to damage, such as scratches or tears. This is particularly true when compared to foam padding. UBL materials may also be lower profile than foam padding, which tends to be somewhat bulky.

In one embodiment, UBL or napped materials with a larger amount of loft may be used. Loft is the thickness of the "fuzzy" or napped part of the unbroken loop material. It is believed that a thicker loft may result in additional resistance to flow or migration of resin. This may be related to the fact that loft creates a layer of air between the fabric and the blank 10; it is believed that this layer of air limits contact between the resin and the outer body of the napped fabric, limiting migration of resin or other hardenable material through the thickness of the fabric to the exterior surface.

As described above, the interior layer 52 may be made of foam padding or other padding in one embodiment. Foam padding, like UBL material, provides resistance to flow or migration of resin; closed-cell foams may be better in this regard than open-cell foams. Foam padding, however, is not optimal for use on the exterior layer 60, as it is easily scratched or damaged. Foam padding does provide a satisfactory level of cushioning for the patient, making the orthopaedic support 15 more comfortable. In one embodiment, the foam padding is between one-eighth (1/8") of an inch and five-eighths of an inch (5/8") thick. One skilled in the art will recognize that many alternatives for both the interior layer 52 and exterior layer 60 exist, such as using a UBL material for an interior layer 52, using foam padding as an exterior layer 60, having both layers made of the same material, using fabrics, plastic sheeting, or other materials for either layer. Suitable foams are commercially available from a number of sources, including Foamex International of Linwood, Pa.

In one embodiment, the orthopaedic support 15 (and thus the interior layer 52, exterior layer 60, and blank 10) has substantially the same shape as the blank 10 described in relation to FIG. 1. In this embodiment, the interior layer 52 and exterior layer 60 may be slightly larger than the blank 10 so the layers can be sealed together at their edges 54 and 66 to create the envelope 50 of the orthopaedic support 15. One skilled in the art will recognize that other shapes, such as those described in relation to FIGS. 2–9, are also suitable and within the scope of the invention. In another embodiment, the envelope 50 of the support 15 has a shape which is different from the shape of the blank 10.

Figure 13:
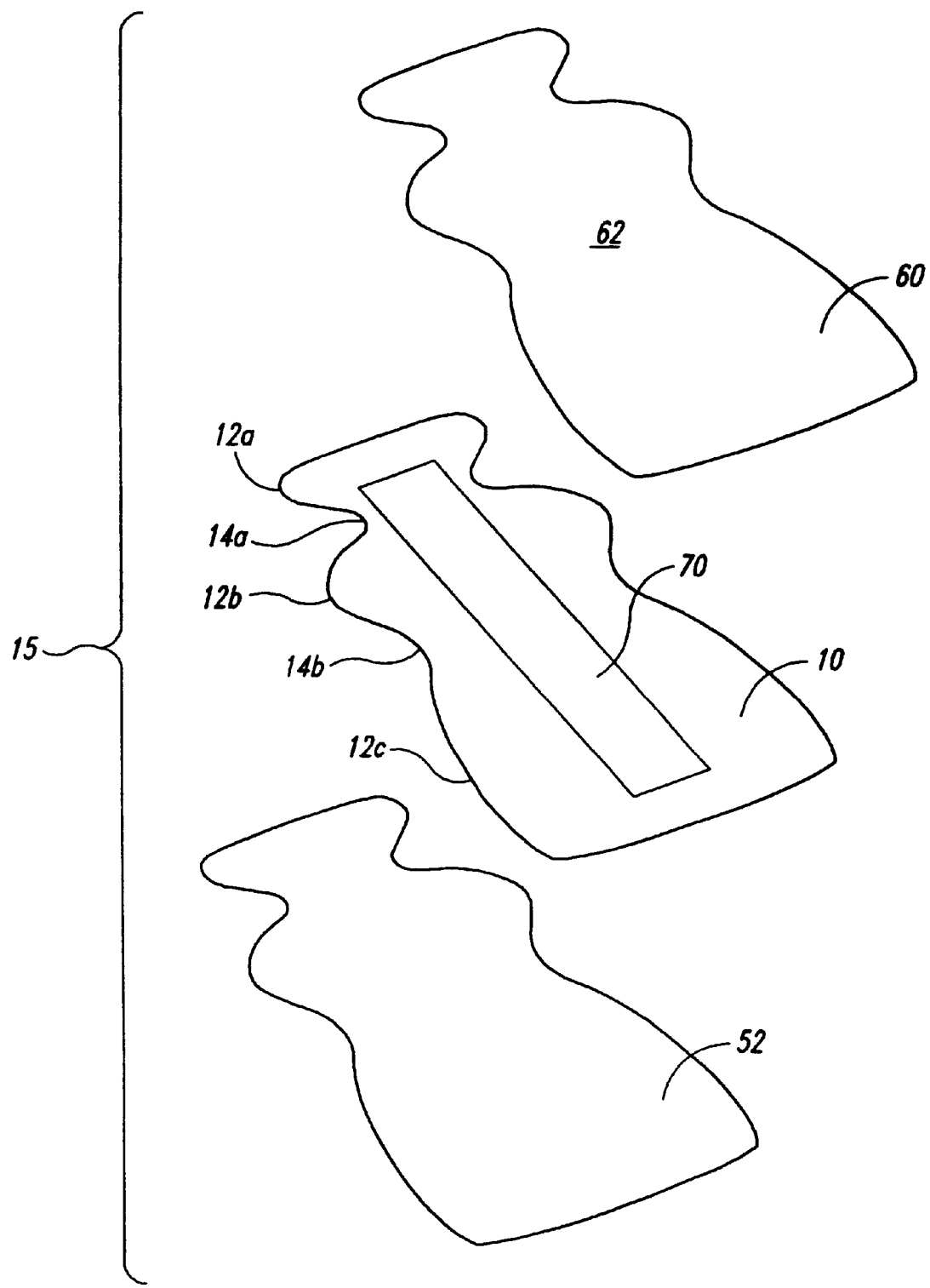
FIG. 13 is an exploded perspective view of an orthopaedic support in one alternative embodiment.

FIG. 13 is an exploded perspective view of the orthopaedic support 15 of FIG. 12. In FIG. 13, the interior layer 52 and the exterior layer 60 form the outer envelope (50 in FIG. 12) of the orthopaedic support 15. The slightly smaller blank 10 fits within the inner and outer layers 52, 60. If so desired, a reinforcement 70 may be included to provide additional stiffness and/or strength to the orthopaedic support 15. The reinforcement 70 may be attached to the blank 10 (such as by an adhesive, etc.) or may otherwise be located within or on the external surface of the envelope 50 of the orthopaedic support 15. In this embodiment, a reinforcement 70 impregnated with a hardenable material is used. This reinforcement 70 provides additional stiffness when the orthopaedic support 15 is hardened for use. The reinforcement 70 can also provide additional high strength fibers, such as fiberglass, to the orthopaedic support 15, which also adds strength and stiffness to the support 15. In one embodiment, the reinforcement 70 may comprise one or more layers of single knit glass and have a rectangular shape, though other shapes may instead be employed. In another embodiment, the reinforcement 70 may comprise an impregnated casting tape having a central area of double-knit type fabric, an exterior layer, an interior layer, and an intermediate open-work matrix of yarns or fibers integrally knit or woven into the fabric and extending between the two layers, where at the edges of the tape the two layers are merged into a single thickness of fabric. One skilled in the art will recognize that many other materials, shapes, and designs may be used for a reinforcement 70 and all are within the scope of the invention.

In one embodiment, the reinforcement 70 extends longitudinally along at least a portion of the structural region (20 in FIGS. 1 and 12, for example), but does not extend into the peripheral region 22. If two or more narrowed joining regions (14 in FIG. 1, for example) are used, the reinforcement may extend longitudinally through all of the joining regions. Looking at FIG. 1A, the reinforcement 70 (not shown in FIG. 1A) may extend proximally along the axis A from a distal end in the distal lobe 12a to a proximal end in the proximal lobe 12c. For example, a rectangular three-inch (3") wide strip of impregnated tape could be used, as well as other shapes and sizes. This additional reinforcement 70 enables the use or narrower joining regions 14 without unduly sacrificing strength and stiffness of the finished article.

In the illustrated embodiment, the reinforcement 70 is an elongate rectangle. Other suitable shapes may instead be employed. If so desired, the reinforcement 70 has a non-rectangular shape. In one embodiment (not shown), the reinforcement 70 has a multiple-lobed design generally corresponding to the arrangement of the blank, with a wider lobe being positioned in one or more of the lobes 12 of the blank and a narrower section being received in one or more of the joining regions 14. It is anticipated that the reinforcement 70 in such an embodiment will be smaller than the blank, though, with the periphery being spaced a fixed or variable distance from the peripheral region 22 of the blank 10.

The reinforcement 70 may be held in place with an adhesive or other attachment, or may also be held in place by the covering materials (e.g., the exterior layer 60). In one embodiment, the reinforcement 70 will bond with the blank 10 as the hardenable material hardens and the two items laminate together, which will also help prevent relative movement between the reinforcement 70 and the blank 10, further strengthening the hardened support.

Exemplary Methods of Manufacture

Orthopaedic supports in accordance with embodiments of the invention may be manufactured in a variety of ways. For ease of understanding, reference is made in the following discussion to the specific support or blank 10 and support 15 shown in FIGS. 1 and 10–13. It should be recognized, however, that aspects of the present invention can be used to manufacture blanks or supports having other shapes and structures, as well.

In one embodiment, a suitable hardenable material is applied to the material from which the support or blank 10 is formed and this material is then cut to the desired non-rectangular shape. If so desired, this cut blank 10 may be used as a support without any additional layers. Alternatively, the blank 10 can be received within an envelope 50 and this assembly can be used as a support 15.

As noted above, though, many of the hardenable materials used in orthopaedic applications are tacky, viscous materials which are not conducive to cutting one blank 10 after another in a commercial production environment. Cutting the desired shapes from continuously coated material essentially necessitates that the entire blank 10 carry the hardenable material and producing a peripheral region which is free from the hardenable material, if such a peripheral region is desired, would be problematic.

In a method in accordance with another embodiment of the invention, the hardenable material is urged under pressure in a molding element to impregnate at least a portion of the flexible material from which the support or blank is formed. This permits relatively complex shapes to be formed from fabric which has not yet been treated with the hardenable material. These shapes may be subsequently impregnated with the hardenable material using the molding element. Alternatively, an excess of the flexible material used to form the support 10 may be placed in the molding element. Only the shape corresponding to a mold shape of the molding element will be impregnated with the hardenable material. Thereafter, excess fabric can be trimmed, leaving an impregnated blank 10 of the desired shape. In this application, the entire blank 10 may be impregnated with the hardenable material.

Figure 14:
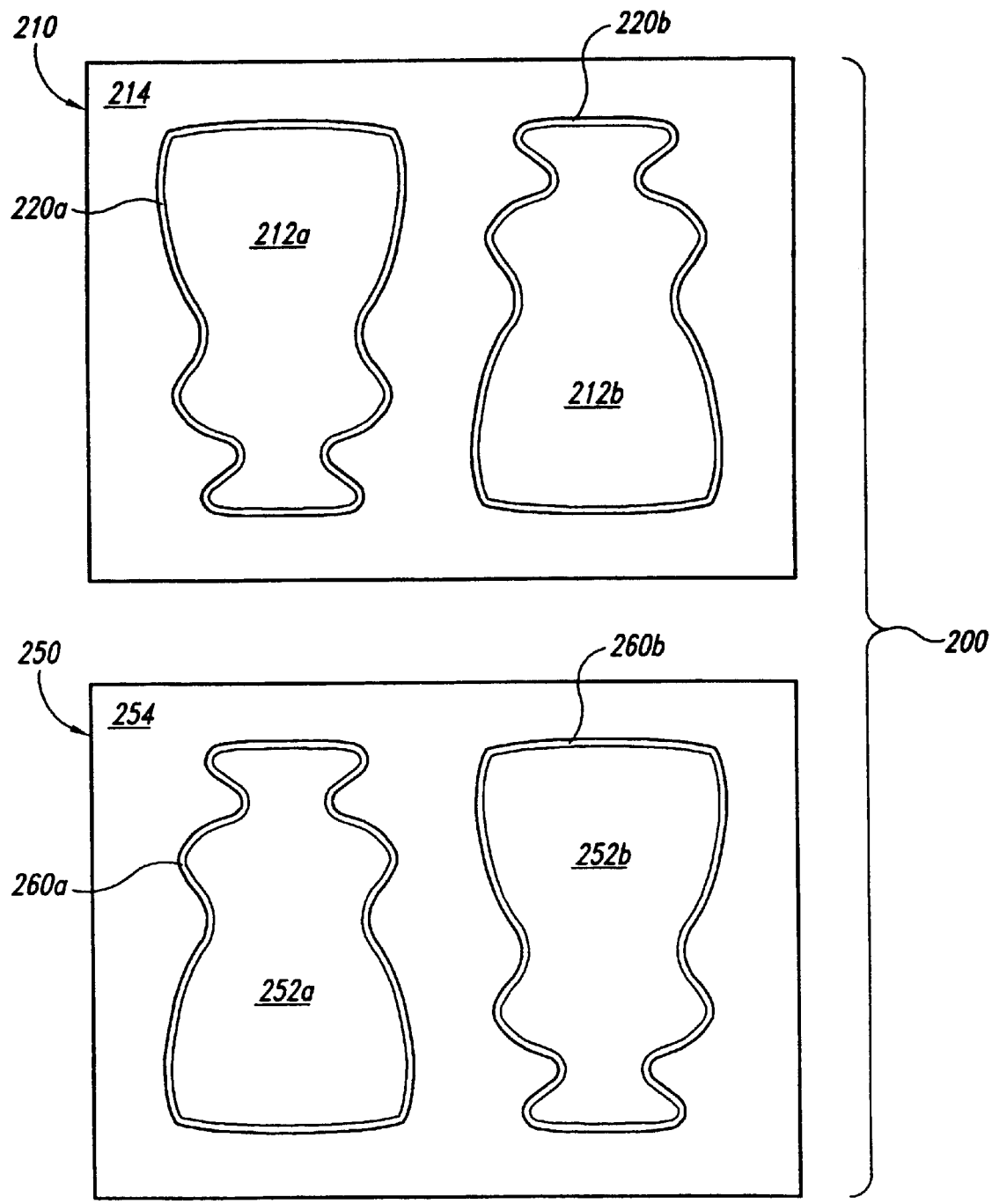
FIG. 14 is a top plan view of a complementary pair of molding members useful in manufacturing the hardenable orthopaedic support of FIGS. 1 and 10.

In an alternative embodiment, a blank 10 is produced with a structural region 20 impregnated with hardenable material and a peripheral region 22 which is free from the hardenable material. FIG. 14 illustrates a molding element 200 which is well-suited for manufacturing such blanks 10 on a commercial scale. The molding element 200 includes a first molding member 210 and a second molding member 250. The illustrated first molding member 210 contains two identical recesses 212a–b which are offset 180° in orientation from one another. Similarly, the illustrated second molding member 250 includes two identical projections 252a–b which are offset 180° in orientation from one another. Each of the projections 252a and 252b of the second molding member 250 is adapted to be received in a complementary recess 212a or 212b, respectively, in the first molding member 210. This enables two supports 10 to be produced in a single operation of the molding element 200. The molding element 200 is not limited to a particular number of pairs of recesses 212 and projections 252, however; molding elements having one or more recess/projection pairs are equally within the scope to the invention. In one embodiment, both of the molding elements 210 and 250 are made out of aluminum, although other materials, e.g., stainless steel or other metals or suitable plastic materials such as HDPE, can be used.

The first molding member 210 has a first confronting face 214 in which the recesses 212 are formed and the second molding member 250 has a second confronting face 254 from which the projections 252 extend. The recesses 212 are adapted to receive a hardenable material, e.g., a water-hardenable or UV-curable resin, therein. Peripheral steps 220a and 220b extend about the peripheries of the recesses 212a and 212b, respectively. These peripheral steps 220 may extend about the entire periphery of the associated recess 212. Alternatively, the peripheral steps may extend about less than the entire recess periphery. Similarly, projection 252a of the second molding member has a peripheral step 260a which extends about at least a portion of the projection periphery and projection 252b has a has a peripheral step 260a which extends about at least a portion of the projection periphery.

Figure 15:
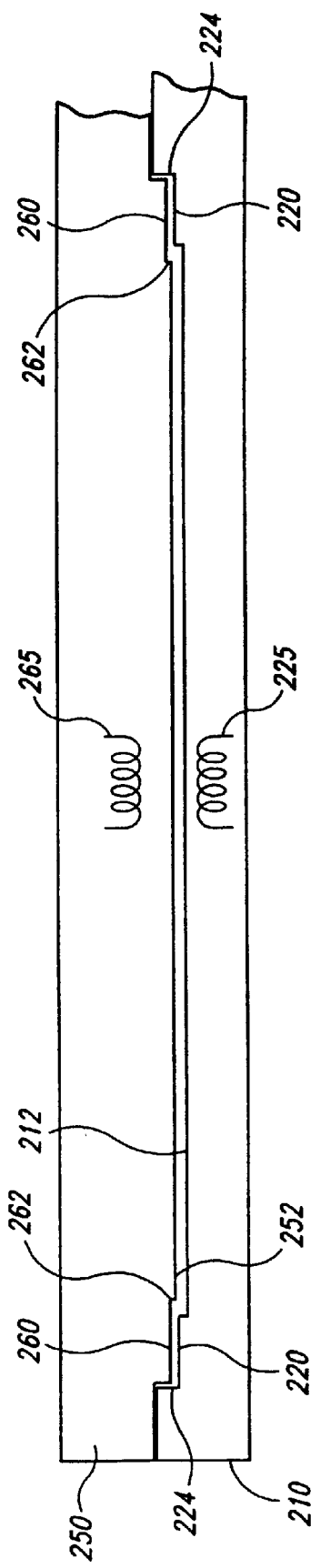
FIG. 15 is a schematic partial cross-sectional view of the molding members illustrated in FIG. 14 juxtaposed with a subassembly of a hardenable orthopaedic support positioned herein.

FIG. 15 schematically illustrates the two molding members 210 and 250 juxtaposed for use. Only one recess 212a and complementary projection 252a is shown; the other recess 212b and projection 252b may have substantially the same shape and are omitted for ease of illustration. As shown in FIG. 15, the peripheral step 220 of the first molding member 210 is recessed from the confronting surface 214 and surrounds the perimeter of the recess 212 and is used to support the peripheral region 22 of a blank 10. The peripheral step 220 helps to contain resin or other hardenable material in the recess 212 during manufacture, as described below. The outer edge of the step 220 is connected to the confronting surface 214 by a substantially perpendicular sidewall 224. The sidewall 224 approximates the perimeter of the intended blank 10. The confronting face 214 may be generally planar and define one plane and the step 220 may be recessed from the confronting face 214 so the step 220 is in a second plane parallel and spaced apart from the first plane. The recess 212 is recessed from the step 220 so as to be in a third plane spaced apart from the first and second planes. The outer surface 214, step 220 and recess 212 are in respective planes that may be substantially parallel to each other and be connected by portions of the first molding member 210 substantially perpendicular to those planes.

The projection 252 projects away from the confronting face 254 of the second molding member 250. The peripheral step 260 of the second molding member 250 is spaced apart from the confronting face 254 and is juxtaposed with the step 220 on the first molding member 210 in manufacturing the blank 10. A forcing surface of the projection 252 is spaced apart from the step 260 and is even further separated from the confronting face 254 than is the step 260. The confronting face 254, peripheral step 260, and forcing surface of the projection 252 may be in three different planes substantially parallel to each other and be connected by portions of the second molding member 250 substantially perpendicular to those planes. The surfaces 252, 254, and 260 of the second molding member 250 correspond in size and pitch to the surfaces 212, 214 and 220, respectively, of the first molding member 210. These surfaces may be substantially level when in use. In an alternative embodiment, the second molding member 250 need not comprise a single contiguous body with a continuous confronting face 254 adapted to closely juxtapose with the confronting face 214 of the first molding member 210. For example, the second molding member 250 may comprise two separate bodies, each of which has the size and shape of one of the projections 252 of the illustrated embodiment. Such an independent member 250 may be used in a manner analogous to a punch in a punch and die operation.

In use, a flexible material to be impregnated may be positioned with respect to one or both of the recesses 212 and/or one or both of the projections 252. If so desired, the flexible material may already be cut to conform to the shape of the sidewall 224 of a single one of the recesses 212. Alternatively, the flexible material may extend outwardly beyond the sidewall 224, e.g., it may take the form of a large rectangle large enough to completely cover one or both of the recesses 212. When the confronting faces 214 and 254 of the first and second molding members 210 and 250, respectively, are juxtaposed, the recessed step 220 of each recess 212 will confront the raised step 260 of the corresponding projection 252. A portion of the oversized sheet of flexible material is received between these steps 220 and 260. This portion of the material may be treated with a flexible adhesive material, such as a flexible synthetic cement, as set forth in copending U.S. application Ser. No. 09/823,968, entitled "Cast Blank Edge Treatment," the entirety of which is incorporated herein by reference. Treating this portion of the fabric with a flexible adhesive or the like can provide a guide for trimming excess fabric from the edges of the blank 10 and will help keep the cut edges from fraying or shedding fibers. Because a flexible adhesive is used, this will not compromise the goal of maintaining a flexible peripheral region 22 of the blank 10.

Before or after the flexible fabric is positioned with respect to the molding members 210 and 250, a quantity of hardenable material, e.g., a water-hardenable resin, can be dispensed into each recess 212 of the first molding member. The quantity of resin placed in the reservoir may be precisely measured to deliver just the amount of resin necessary to suitably impregnate the structural region 20. Depending on the nature of the resin, it may be advantageous to heat the resin to reduce its viscosity, e.g., by heating one or both of the molding members 210 and 250. FIG. 15 schematically illustrates a heat source for each of the molding members 210 and 250 as electrical resistance heaters 225 and 265, respectively, but any suitable heat source may be employed. To impregnate the resin into the spacer, the projections 252 of the second molding member 250 are brought into alignment with the corresponding recesses 212 of the first molding member 210 and the first and second molding members 210 and 250 are urged toward one another. This squeezes the resin between a projection 252 and the corresponding recess 212, impregnating the resin into the fabric. The resin need not be placed under pressure by squeezing the two molding members together. In another embodiment (not shown), a flexible membrane may extend over the top of the peripheral step 220 and the recess 212 of the first molding member 210 and be sealed against the confronting face 214. By drawing a vacuum on the recess 212, the membrane will be drawn toward the bottom of the recess, placing the resin under sufficient pressure to allow it to impregnate the fabric.

In the illustrated molding element 200, the peripheral region 22 of the fabric is received between the peripheral steps 220 and 260 and may be squeezed therebetween when the molding members 210 and 250 are urged toward one another. This will limit the ingress of resin from the recess 212 into the peripheral region 22. If a flexible adhesive or the like is applied to the peripheral region 22, as noted above, forcing the molding members 210 and 250 toward one another will also squeeze the flexible adhesive to drive it into the peripheral region of the fabric. In an alternative embodiment, the adhesive may be applied to the peripheral region 22 and allowed to cure before the and the fabric may be trimmed to the desired blank size before the fabric is placed in the molding element 200. The presence of the flexible adhesive may further restrict movement of hardenable resin from the recess 212 into the peripheral region 22 of the blank 10.

By way of example, in manufacturing an orthopedic support 10 for a patient's upper extremity, approximately 43 grams of resin, plus or minus 1 gram, may be used for each edge-treated and cut support 10. The amount of resin may vary depending on the dimensions of the orthopaedic support 10, though. The molding members 210 and 250 and the resin are preferably heated to between 140 to 160 degrees Fahrenheit, but other temperature ranges are also within the scope of the invention. The flexible fabric is placed into the recess 212 of the first molding member 210 and the structural region of the fabric is held adjacent to, or in contact with, the resin. The molding members 210 and 250 may be forced together by a machine applying a force of approximately 70 pounds per square inch ("psi") for between 30 and 60 seconds. Other ranges of pressure and time are within the scope of the invention. This forces a large percentage of the resin into the structural region 20 of the fabric, which ultimately will provide it with its stiffness when it is hardened.

After the allotted time has passed, the molding members 210 and 250 may be separated and the resin-impregnated blank 10 can be removed from the molding element 200, for example by a gloved hand. If the blank 10 is to be used as a support, it may be packaged in water vapor-impermeable packaging. If the blank 10 is to be used in manufacturing a more complex structure such as that of the support 15 of FIG. 12, the blank 10 may be positioned between an inner layer 52 and an exterior layer 60 and those two layers 52 and 60 may be bonded to one another to create the envelope 50 within which the blank 10 is received.

It is to be understood that the foregoing detailed description and the accompanying drawings relate to some of the potential embodiments of the invention. Further modifications and variations of the present invention are contemplated. For example, with regard to materials which may be used, one or both of the outer layers of the double-knit-type material may be of high strength material, such as fiberglass, aramids such as kevlar, or other high strength fibers or materials. The spacer yarns, and one of the two outer layers may be formed of polypropylene, polyester, nylon, or a high-strength material, e.g., fiberglass or aramids such as kevlar. Other materials and yarns may also be used.

It is further noted that the properties of the double-knit-type knit-type casting material may be changed as desired by (1) altering filament size of the surface yarns or spacer yarns, (2) changing the type of surface knits, (3) changing the density of spacer yarns, (4) interweaving stretchable yarns such as lycra to increase conformability and recovery, and (5) selectively inlaying high strength fibers such as carbon, kevlar or the like. It is also noted that flat or contoured casting blanks may be knit in a completed form so that the steps of cutting the material and securing against fraying may be avoided. In addition, hardenable material other than water-hardenable material may be employed in combination with an appropriate activating agent, e.g., ultraviolet radiation for UV-curable materials or a second component of an epoxy or other known two-part polymer hardening systems. Concerning the thickness of the double-knit type material, it may range from 1/32 of an inch up to 1/2-inch or even one inch in thickness depending on the conformability and strength which is required or desired.

Moreover, all of the disclosed embodiments may be of variable thickness to provide selected areas of increased strength or of increased conformity to bodily configurations. It is also noted that all of the embodiments of the invention may be provided with the moisture impermeable packaging to avoid hardening of the supports or splints prior to use, while in storage, on sale, or the like.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "above," "below," and words of similar import, when used in this application, shall refer to this application as a whole and not to any particular portions of this application. Use of the term "or," as used in this application with respect to a list of two or more items, shall be interpreted to cover any, all, or any combination of items in the list.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

Incorporated in their entirety by reference are the following U.S. applications, which are assigned to the assignee of this application: application Ser. No. 10/136,026, entitled "Hardenable Orthopaedic Supports," filed concurrently herewith; and application Ser. No. 10/136,458, entitled "Hardenable Orthopaedic Supports," filed concurrently herewith. Aspects of the invention can be modified, if necessary, to employ the systems, functions and concepts of the various patents and applications described above to provide yet further embodiments of the invention.

The above detailed descriptions of embodiments of the invention are not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while steps are presented in a given order, alternative embodiments may perform routines having steps in a different order. The teachings of the invention provided herein can be applied to other devices and/or systems, not necessarily the system described herein. These and other changes can be made to the invention in light of the detailed description. The elements and acts of the various embodiments described above can be combined to provide further embodiments.

These and other changes can be made to the invention in light of the above detailed description. In general, the terms used in the following claims, should not be construed to limit the invention to the specific embodiments disclosed in the specification, unless the above detailed description explicitly defines such terms. Accordingly, the actual scope of the invention encompasses the disclosed embodiments and all equivalent ways of practicing or implementing the invention under the claims.

While certain aspects of the invention are presented below in certain claim forms, the inventors contemplate the various aspects of the invention in any number of claim forms. Accordingly, the inventors reserve the right to add additional claims after filing the application to pursue such additional claim forms for other aspects of the invention.

We claim:

1. A hardenable orthopaedic support assembly comprising:
  a flexible padding first layer having an outer edge portion;
  a second layer of napped material having a napped side and an outer edge portion, the napped side facing towards the layer of padding material, wherein the outer edge portion of the second layer is at least partially attached to the outer edge portion of the first layer;
  a blank comprising a flexible material which is at least partially impregnated with a hardenable material, the blank being located between the first layer and the second layer; and
  said layer of napped material being substantially free of impregnated hardenable material except locally where said napped material touches said blank.

2. The orthopedic support assembly of claim 1 wherein the flexible material comprises a double layer knit fabric having spaced interwoven layers, an open-work matrix of fibers interconnecting the interwoven layers, and the open-work matrix of fibers is impregnated with the hardenable material.

3. The orthopaedic support assembly of claim 2 wherein the open-work matrix of fibers of the double layer fabric provides support resulting from the hardening of a hardenable material.

4. The orthopaedic support assembly of claim 1 wherein the flexible material comprises a fabric.

5. The orthopaedic support assembly of claim 1, further comprising a water vapor impermeable package adapted to enclose the layers of padding material and napped material and the blank.

6. The orthopaedic supped assembly of claim 1 wherein the flexible material comprises a double layer knit fabric having spaced interwoven layers, an open-work matrix of fibers interconnecting the interwoven layers, and wherein further at least one of the interwoven layers of the double layer fabric is at least partially composed of high strength fibers.

7. The orthopaedic support assembly of claim 1 wherein the flexible material comprises a double layer knit fabric having spaced interwoven layers, an open-work matrix of fibers interconnecting the interwoven layers, and wherein further at least one of the layers of the double layer fabric is at least partially composed of fiberglass.

8. The orthopaedic support assembly of claim 1 wherein to flexible material comprises a double layer knit fabric having spaced interwoven layers, an open-work matrix of fibers interconnecting the interwoven layers, and wherein further at least one of the layers of the double layer fabric is at least partially composed of aramid fibers.

9. The orthopaedic support assembly of claim 1 wherein the flexible material comprises a double layer knit fabric having spaced interwoven layers, an open-work matrix of fibers interconnecting the interwoven layers, and wherein further at least one of the layers of the double layer fabric is at least partially composed of carbon fibers.

10. The orthopaedic support assembly of claim 1 wherein the layer of padding material is foam padding.

11. The orthopaedic support assembly of claim 1 wherein the layer of padding material is foam padding that is between 0.1 inch and 0.5 inch thick.

12. The orthopaedic support assembly of claim 1, further comprising a reinforcement located between the layers of napped material and the padding material.

13. The orthopaedic support assembly of claim 1, further comprising a reinforcement located between the layers of napped material and the padding material, the reinforcement being composed at least partially of a second double layer fabric having spaced second interwoven layers and a second open-work matrix of fibers interconnecting the second interwoven layers.

14. The orthopaedic support assembly of claim 1, further comprising a reinforcement located between the layers of napped material and the padding material, the reinforcement being composed of a single knit glass material.

15. The orthopaedic support assembly of claim 1, further comprising a reinforcement located between the layers of napped material and the padding material, the reinforcement being impregnated with a hardenable material.

16. The orthopaedic support assembly of claim 1 wherein the napped material is an unbroken loop material.

17. The orthopaedic support assembly of claim 1 wherein the layer of napped material has a substantially smooth side, the substantially smooth side facing away from the blank.

18. An assembly as defined in claim 1 wherein the napped layer is the outermost layer of the assembly.

19. A hardenable orthopaedic support assembly comprising:
   a flexible padding first layer having an outer edge portion;
   a second layer of high loft material having a high loft side and an outer edge portion, the high loft side facing towards the layer of padding material, wherein the outer edge portion of the second layer is at least partially attached to the outer edge portion of the first layer;
   a blank comprising a flexible material which is at least partially impregnated with a hardenable material, the blank being located between the first layer and the second layer; and
   said layer of high loft material being substantially free of impregnated hardenable material except locally where said high loft material engages said blank.

20. An assembly as defined in claim 19 wherein the layer of high loft material is the outermost layer of said assembly.

21. A hardenable orthopaedic support assembly comprising:
   a non-rectangular body comprising a double layer fabric having a first interwoven layer, a second interwoven layer spaced apart from the first layer; and a matrix of filaments interconnecting the first and second interwoven layers, at least a portion of the fabric being impregnated with a water-hardenable material;
   a separately, formed reinforcement carried on the body, the reinforcement including a fabric and a water-hardenable material, the reinforcement covering substantially less than an entire surface area of the first interwoven layer; and
   the non-rectangular body comprising at least two lobes connected by a narrower joining region and the reinforcement has a generally rectangular shape extending along said body through said narrower region but not laterally into said lobes.

22. A hardenable orthopaedic support assembly comprising:
   a layer of padding material having an outer edge portion;
   a layer of unbroken loop material having a substantially smooth side, a napped side, and an outer edge portion, the substantially smooth side facing away from the layer of padding material, wherein the outer-edge portion of the layer of unbroken loop material and the outer edge portion of the layer of padding material are at least partially attached;
   a blank made of a permeable, flexible material, the flexible material comprising a double layer knit fabric having spaced interwoven layers, an open-work matrix of fibers interconnecting the interwoven layers, wherein further the open-work matrix is at least partially impregnated with a hardenable material;
   the blank being located between the layer of unbroken loop material and the layer of padding material; and
   said layer of unbroken loop material being substantially free of impregnated hardenable material except locally where said unbroken loop material touches said blank.

23. An assembly as defined in claim 22 wherein said unbroken loop material is the outermost layer of said assembly.

24. A hardenable orthopaedic support assembly comprising:
   a layer of padding material having an outer edge portion;
   a layer of napped material having a substantially smooth side, a napped side, and an outer edge portion, the substantially smooth side facing away from the layer of padding material, wherein the outer edge portion of the layer of napped material and the outer edge portion of the layer of padding material are at least partially attached;
   a blank comprising a flexible material which is at least partially impregnated with a hardenable material, the blank being located between the layer of napped material and the layer of padding material;

wherein the layers of padding material and napped material and the blank are shaped to cover at least a portion of a patient's anatomy, and wherein further the shape includes two or more lobes and one or more narrowed joining regions, the lobes adapted to be located near a particular part of the patient's anatomy; and said layer of napped material being substantially free of hardenable material except locally where the napped material touches said blank.

25. An assembly as defined in claim 24 wherein the layer of napped material is the outermost layer of said assembly.

26. An assembly as defined in claim 24 wherein the napped layer is the outermost layer of the assembly.

27. A hardenable orthopaedic support assembly comprising:

a non-rectangular body comprising a double layer fabric having a first interwoven layer, a second interwoven layer spaced apart from the first layer; and a matrix of filaments interconnecting the first and second interwoven layers, at least a portion of the fabric being impregnated with a water-hardenable material;

a separately formed reinforcement carried on the body, the reinforcement including a fabric and water-hardenable material, the reinforcement covering substantially less than an entire surface area of the first interwoven layer;

said non-rectangular body having a principal longitudinal extent and laterally extending peripheral areas;

said reinforcement being in the form of a strip extending along said principal longitudinal extent but not to said peripheral areas; and said reinforcement strip being bonded to said non-rectangular body.

\* \* \* \* \*

UNITED STATES PATENT AND TRADEMARK OFFICE
CERTIFICATE OF CORRECTION

PATENT NO. : 6,824,522 B2 Page 1 of 1
DATED : November 20, 2004
INVENTOR(S) : Wendy Henderson et al.

It is certified that error appears in the above-identified patent and that said Letters Patent is hereby corrected as shown below:

Column 1,
Line 25, after "calcined gypsum" continue with -- For example, -- (not a new paragraph).

Column 2,
Line 29, delete "our" and insert -- outer --.

Column 12,
Line 54, delete first occurrence of "has a".

Column 17,
Line 5, delete "supped" and insert -- support --.

Signed and Sealed this

Third Day of May, 2005

JON W. DUDAS
*Director of the United States Patent and Trademark Office*